United States Patent [19]

Lewis

[11] 4,452,515
[45] Jun. 5, 1984

[54] EYE TESTING DEVICE

[75] Inventor: Walter M. Lewis, Provo, Utah

[73] Assignee: Stereo Optical Company, Inc., Chicago, Ill.

[21] Appl. No.: 343,275

[22] Filed: Jan. 27, 1982

[51] Int. Cl.³ .............................................. A61B 3/02
[52] U.S. Cl. .................................... 351/243; 351/222
[58] Field of Search ............... 351/222, 239, 243, 244, 351/245

[56] References Cited

U.S. PATENT DOCUMENTS 1,669,916  5/1928  Smith .
1,949,067  2/1934  Wheelock et al. .
3,012,472  12/1961  Feinberg et al. .
4,027,954  6/1977  Good .............................. 351/222 X Primary Examiner—John K. Corbin
Assistant Examiner—Rodney B. Bovernick
Attorney, Agent, or Firm—Lockwood, Dewey, Alex & Cummings

[57] ABSTRACT

An improved eye testing apparatus is provided which permits the operator thereof to precisely and clearly designate certain characters of the eye test pattern. The device includes an external stage, a duplicate test pattern on the stage, and a mask having separate designation locations for designating a character of the test pattern at a vision station within the device while simultaneously designating an identical character of the duplicate test pattern.

13 Claims, 4 Drawing Figures

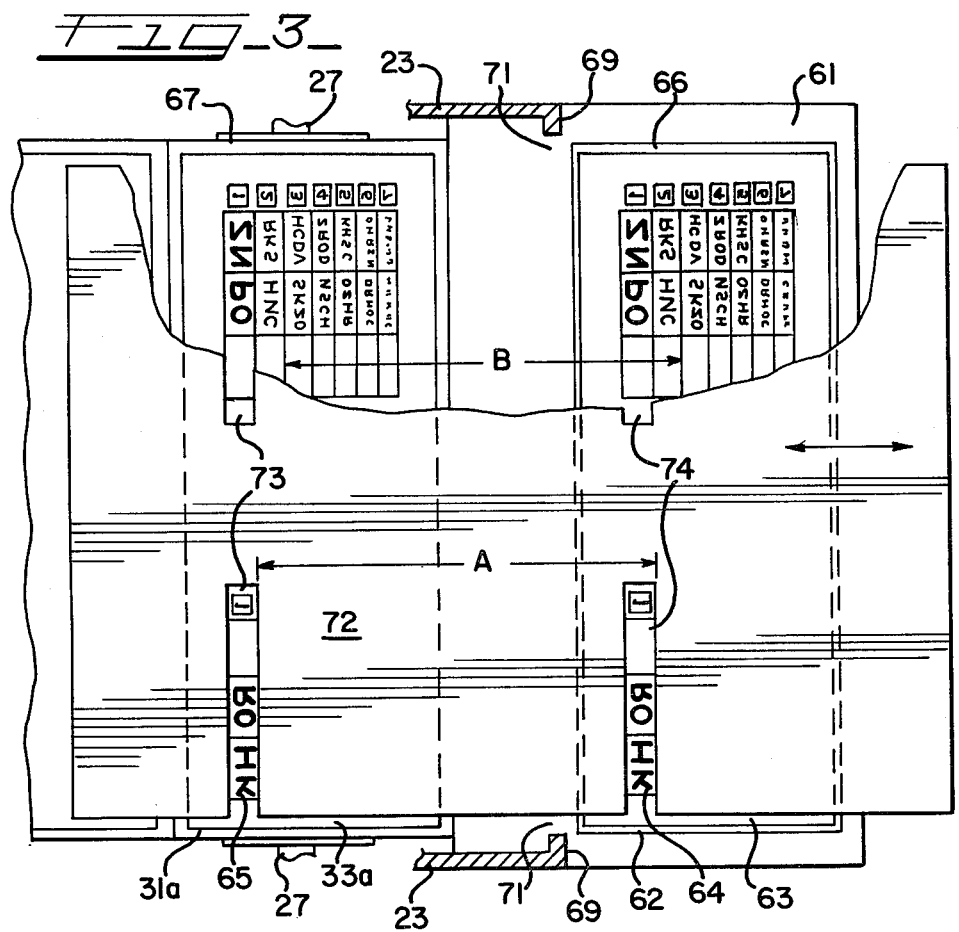
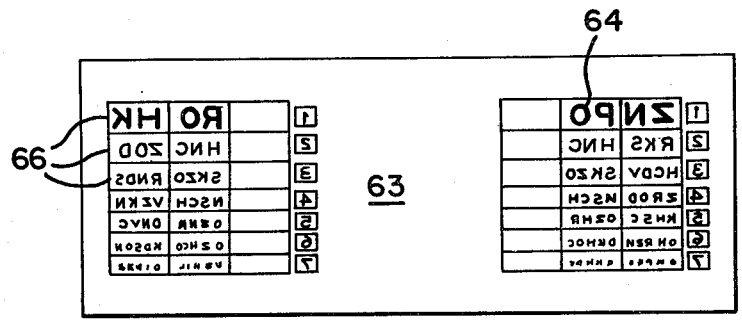

EYE TESTING DEVICE

BACKGROUND AND DESCRIPTION OF THE INVENTION

This invention generally relates to an eye testing device by which the individual being tested is asked to identify certain characters of an eye test pattern, and more particularly to a device by which selected characters or portions of the eye test pattern within the device are readily, accurately and clearly designated by means of structure that is located outside of the enclosed casing of the device.

Compact eye testing devices are well-known for use in conducting limited testing of opthalmic abilities of individuals. Such devices are particularly well suited for administering drivers license vision tests and for quickly checking the vision of large numbers of students, including relatively young students. Devices of this type are of a general character such as described in U.S. Pat. No. 3,012,472. In such devices, a vision test pattern is located within an enclosed casing, which casing has means for illuminating and viewing the test pattern. The actual vision testing is accomplished by asking the individual being tested to identify certain characters, typically a line of alphabet letters.

A common difficulty that is often encountered by the operator conducting vision tests on these types of devices is with respect to the means by which the operator must indicate to the individual being tested exactly which character or characters the operator is requesting to be identified by the person being tested. Typically, in devices of this type, the person administering the vision test inserts an elongated pointer into the device through an opening in the wall thereof and asks the person being tested to identify the characters designated by the pointer. Usually, the test administrator will first point to characters of the largest type size on the test pattern and gradually indicate characters of smaller type size until the characters are no longer legible to the person being tested.

A principle difficulty of this direct pointing approach is that the pointer or other indicator means often obscures the characters being indicated and/or does not precisely designate the desired characters, leading to confusion and error, especially when the individual being tested is a young child. Another related difficulty that is often evident while using such devices is caused by the fact that the test pattern is not readily visible or directly visible by the operator who must look through an opening in the side of the device, which is both difficult and fatiguing. This, too, can lead to error and an inaccurate vision test.

These difficulties are solved by the present invention by modifying these types of devices to include a duplicate test pattern on a stage that is exterior to the device within which the interior illuminated test pattern is located. Provided in association with the stage and the interior test pattern, is masking means for simultaneous designation of identical characters on both the interior and the exterior test patterns, which designation is accomplished through manipulation of the mask of the operator, which manipulation takes place on the external stage.

It is accordingly a general object of this invention to provide an improved eye testing device.

Another object of the present invention is an improved eye testing method and device by which the characters to be identified by the person being tested are designated without the use of a pointer or the like.

Another object of the present invention is an improved vision testing device and method that includes means for remotely designating test characters in a precise and accurate manner.

These and other objects of the present invention will be apparent from the following description and from the drawings in which:

FIG. 3 is an enlarged view along the line 3—3 of FIG. 2; and

FIG. 4 is a detail view of a test pattern or object containing typical characters to be identified during vision testing.

Figure 1:
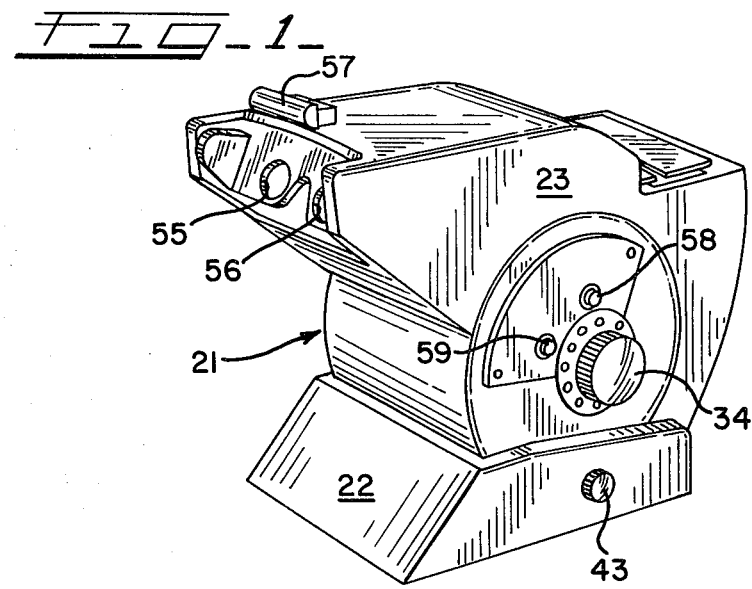
FIG. 1 is a perspective view of the preferred device according to this invention.
Figure 2:
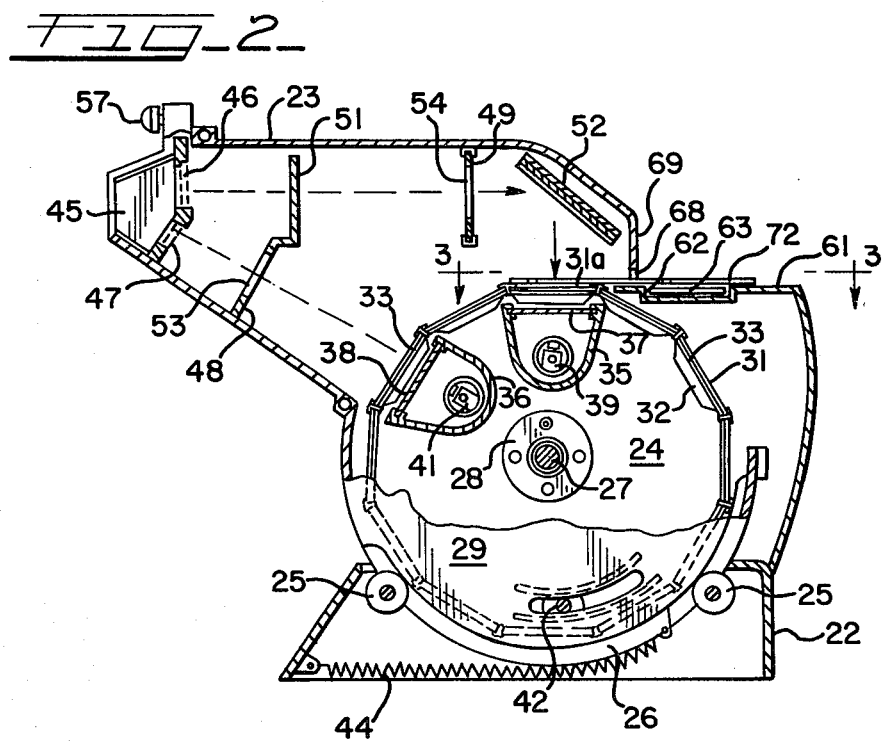
FIG. 2 is a longitudinal sectional view of the device illustrated in FIG. 1.

The device according to this invention, generally designated as 21, includes a base member 22, a casing 23, and a rotatable drum member 24 which is supported on the base member 22 by rotation means such as guide rollers 25 within a guideway 26. The drum member 24 is mounted to the casing 23 by means of a shaft 27 mounted to hubs 28 in the side walls 29 of the casing 23.

Rotatable drum member 24 includes a plurality of rectangular apertures 31 that are circumferentially disposed thereon, each aperture 31 being associated with a holder means 32 for positioning and securing an internal test pattern 33 at each aperture 31. Each internal test pattern 33 is typically a pair of slide transparencies that are positioned and mounted so as to effect a stereo image that is well suited for checking vision quality and capability. A position indicating dial 34 is mounted onto the shaft 27, and the operator rotates the drum member 24 by turning the dial 34 in order to position a particular internal test pattern 33 at a desired location within the casing 23 along the circumference of the drum member 24.

A far point test station 35 and a near point test station 36 are mounted within the casing 23 interior of the disk member 24, each such test station 35, 36 having a window, 37, 38 and an illuminating means 39, 41, respectively. If desired, each test station 35 or 36 may have dual windows, illuminating means, and compartments housing same in order to enhance the stereo effect. By moving the position indicating dial 34, the operator can align a selected internal test pattern 33 with either the far point test station 35 or the near point test station 36, and this location can be secured by means of a lug and shaft means 42 having a tension control knob 43, typically in association with a tension spring 44. The structural features of the operation of the drum member 23 with respect to the test stations 35 and 36, as well as other features of the device, are generally in accordance with those of U.S. Pat. No. 3,012,472, incorporated by reference hereinto.

A viewing means 45 is positioned at a location of the casing remote from the test stations 35 and 36, the viewing means including a far point lens system 46 and a near point lens system 47. Positioned between the near point lens system 47 and the near point test station 36 is a near point divider member 48 for assisting in maintaining the integrity of the line of sight between the near point lens system 47 and the near point test station 36. Positioned between the far point lens system 46 and the far point test station 35 is a far point divider member 49. A septum 51 to facilitate fusion of the slides for a stereo optical effect is positioned between the far point divider member 49 and the far point lens system 46. An optical means 52 is located along the line of sight between the far point divider member 49 and the far point test station 35. Typically, the optical means 52 is in the form of a highly reflective surface such as a mirror that is visually aligned with the far point lens system 46 so that the plane of the internal test pattern or target slide transparency 33 that is aligned with the far point test station 35 will be substantially normal to the line of sight.

With more particular reference to the near point divider member 48 and the far point divider member 49, each has a pair of openings 53, 54. The openings 53 are in alignment with the near point lens system 47 and serve as separate apertures for defining the field of vision for the near point stereo testing. The pair of openings 54 are in alignment with the far point lens system 46 and serve as separate apertures for defining the far field of stereo vision. The septum 51 assists in optically merging the stereo test object components or characters located at the far point test station 35.

The person being tested looks through viewing openings 55, 56 of the viewing means 45, typically while resting his or her head against a forehead rest 57. When the operator of the device 21 wishes to have the person being tested view the pair of stereo side transparencies or internal test pattern 33 at the near point test station 36, the operator turns on the near point illuminating means 41 by the operation of suitable circuitry (not shown) while the far point illuminating means 39 remains unlit, with the result that the viewer's line of vision will be automatically directed to the near point test station 36. Likewise, when the operator wishes to have the person being tested view the pair of stereo slide transparencies or internal test pattern 33 at the far point test station 35, the far point illuminating means 39 is lit, while the near point illuminating means is unlit. As a means for assisting the operator, the rotatable drum member 24 can include a pair of openings within which are typically mounted a far point indicator lens 58 and a near point indicator lens 59. When the device 21 is in its far point viewing mode, light from the far point illuminating means 39 will be visible through the far point indicator lens 58, while the near point indicator lens 59 will remain dark. Putting the device 21 in its near point vision testing mode will permit the operator to observe light from the near point illuminating means 41 through the near point indicator lens 59, while the far point indicator lens 58 remains darkened.

The casing 23 has a stage area or member 61 that is external of the casing and of the rotatable drum member 24 therewithin. In the preferred embodiment of the apparatus illustrated in the drawings, the stage member 61 lies in a plane that is generally parallel to one of the rectangular apertures 31, the one that is selected for and that is positioned at the far point test station 35, this particular far point rectangular aperture being designated as 31a, it being understood that this will be a different aperture 31 depending upon the selection made by operation of the position indicating dial 34.

Stage member 61 includes an external test pattern 63, preferably mounted within a recess 62 of the stage member 61. External test pattern 63 includes characters 64 that are identical to, and that are arranged in a sequence the same as, characters 65 on the internal test pattern 33 at the far point rectangular aperture 31a. Typically, the external test pattern 63 will be of substantially the same shape, size, and layout as the stereo slide transparency internal test pattern 33, although the sizing and positioning could be somewhat different, provided there is a direct relationship between the spacing between the lines 66 of the external test pattern 63 and similar lines of characters 67 of the stereo slide transparency internal test pattern 33. A slot 68 is provided in said casing 23 at a location through a wall member 69 of the casing 23 that is adjacent to the stage member 61, preferably such that the stage member 61 provides an edge 71 of the slot 68.

A mask member 72 overlies both the rectangular aperture 31a and the stage member 61, whereby the mask member 72 occludes substantially all of both the external test pattern 63 and the stereo slide transparency internal test pattern 33 at the far point rectangular aperture 31a. The mask member 72 includes one pair of designation areas 73 for overlying a portion of the stereo slide transparency internal test pattern 33a, and another pair of designation areas 74 overlying a portion of the external test pattern 63. Usually, the designation areas 73, 74 will take the form of slots within the mask member 72, and the mask member 72 will be opaque, with the result that the mask member 72 will fully occlude all of the characters 64 on the external test pattern 63 and all of the characters 65 on the stereo slide transparency internal test pattern 33a, except for those characters 64, 65, respectively, which the operator desires to have the person being tested attempt to identify in order to administer the vision test.

The designation areas 73, 74 are positioned from one another such that the characters 64 highlighted or designated by the designation areas 74 are identical to the characters 65 that are highlighted or designated by the designation areas 73. In this regard, the distance "A" between the pairs of slots 73 and the pairs of slots 74 is substantially identical to the distance "B" between the lines of characters 66 and the lines of characters 67. By this structure, the operator is able to slide the mask member 72 along the stage member 61 in order to highlight or designate which characters 65 are made visible or highlighted by the one pair of designation areas 73, while simultaneously viewing or highlighting those same characters or groups of characters by means of the pair of designation areas 74. In this way, the operator precisely designates those characters 65 that are to be identified by the person being tested without any possibility of confusion or uncertainty and with obscuring any portion of the characters designated on the stereo slide transparency internal test pattern 33a.

Although it is preferred that the mask member 72 be opaque and that the designation areas 73, 74 be in the form of slots, it is also possible to have the mask member 72 be of a darkened, but not opaque, character, while the designation areas 73, 74 could be made of a transparent film or other material that is lighter or brighter than such a mask member 72, whereby the selected characters are highlighted or otherwise readily distinguished from the rest of the characters of the stereo slide transparency internal test pattern 33a and/or the external test pattern 63.

This invention can be embodied in various forms and, therefore, is to be construed and limited only by the scope of the appended claims.

I claim:

1. In a vision testing apparatus including: a base, a light-occluding casing carried by said base;

a drum member rotatably supported in said casing, means for rotating said drum member, said drum member having a periphery, said drum member having a vision test station disposed along said periphery of the drum member;

an internal test pattern carried by said drum member in position to be selectively moved into alignment with the vision test station, said internal test pattern having a plurality of characters;

viewing means carried by said casing including lens means adapted for optical alignment with said internal test pattern, the improvement comprising:

a stage member external to said casing;

an external test pattern, said external test pattern being supported by said stage member and having characters that are substantially identical to the internal test pattern characters;

a slot in said casing, said slot being between said stage member and said vision test station on said drum member;

remote designation means for simultaneously designating at least a certain one of the characters of said internal test pattern while simultaneously designating at least a certain one of the characters of said external test pattern, said certain character of the internal test pattern being the same as said certain character of the external test pattern; and said remote designation means includes a mask member overlying at least a portion of said stage member and at least a portion of said vision test station, said mask member having a one area and another area for simultaneously designating said certain character of the internal test pattern and said certain character of the external test pattern while simultaneously occluding portions of the internal and external test patterns other than said certain character.

2. The vision testing apparatus of claim 1, wherein said mask member is slidably mounted on said stage member and through said slot.

3. The vision testing apparatus of claim 1, wherein said external test pattern is substantially identical in content to said internal test pattern.

4. The vision testing apparatus of claim 1, wherein said internal test pattern includes said characters on a slide transparency and wherein said external test pattern includes said characters on a printed type of pattern.

5. The vision testing apparatus of claim 1, wherein said vision test station includes illumination means.

6. The vision testing apparatus of claim 1, wherein said stage member lies in a plane that is generally parallel to said vision test station.

7. The vision testing apparatus of claim 1, wherein said external test pattern lies in a plane that is generally parallel to said internal test pattern.

8. The vision testing apparatus of claim 1, wherein said stage member includes a recess, and said external test pattern is located within said recess.

9. The vision testing apparatus of claim 1, wherein said characters of the external test pattern are substantially identical to and are arranged in the same sequence as said characters of the internal test pattern.

10. The vision testing apparatus of claim 1, wherein said external test pattern is of substantially the same shape, size and layout as said internal test pattern.

11. The vision testing apparatus of claim 1, wherein said remote designation means includes a mask member that overlies at least a portion of said stage member and at least a portion of said vision test station, said mask member has a slot overlying said internal test pattern, said mask member has another slot overlying said external test pattern, and said mask member is generally opaque at locations other than said slots.

12. The vision testing apparatus of claim 1, wherein said internal test pattern characters are structured as lines of characters, said external test pattern characters are structured as lines of characters substantially identical to respective ones of said internal test pattern lines of characters, said remote designation means includes a mask member having slots, said slots are spaced apart by a preselected distance, and said preselected distance is substantially the same as the distance between said respective lines of characters of the internal and external test patterns.

13. The vision testing apparatus of claim 1, wherein said remote designation means includes a mask member that overlies at least a portion of said internal test pattern and at least a portion of said external test pattern, said mask member has generally transparent designation areas, one designation area overlying a portion of said internal test pattern and another designation area overlying a portion of said external test pattern, and said mask member is less transparent than said designation areas at locations other than said designation areas.

* * * * *